United States Patent
Bach

(10) Patent No.: US 6,933,141 B1
(45) Date of Patent: Aug. 23, 2005

(54) ENZYME GRANULATE

(75) Inventor: Poul Bach, Birkerød (DK)

(73) Assignee: Novozymes A/S, Bagsvaerd (DK)

( * ) Notice: Subject to any disclaimer, the term of this patent is extended or adjusted under 35 U.S.C. 154(b) by 306 days.

(21) Appl. No.: 09/675,952

(22) Filed: Sep. 29, 2000

Related U.S. Application Data

(60) Provisional application No. 60/185,206, filed on Feb. 25, 2000, and provisional application No. 60/158,270, filed on Oct. 7, 1999.

(30) Foreign Application Priority Data

| Oct. 1, 1999 | (DK) | 1999 001415 |
| Feb. 17, 2000 | (DK) | 2000 00251 |

(51) Int. Cl.⁷ .............................. C12N 9/98; C12N 9/00
(52) U.S. Cl. ....................................... 435/187; 435/183
(58) Field of Search ................................. 435/183, 187

(56) References Cited

U.S. PATENT DOCUMENTS

| 4,016,040 | A |   | 4/1977  | Win et al. |
| 4,106,991 | A |   | 8/1978  | Markussen et al. |
| 4,707,287 | A | * | 11/1987 | Herdeman |
| 4,713,245 | A |   | 12/1987 | Ando et al. |
| 5,230,822 | A | * | 7/1993  | Kamel et al. |
| 5,846,798 | A | * | 12/1998 | Paatz et al. .................. 435/187 |

FOREIGN PATENT DOCUMENTS

| EP | 0 170 360 B1 | 2/1986 |
| EP | 0 170 360 | 5/1986 |
| EP | 0 304 331 | 2/1989 |
| EP | 0 304 331 B1 | 2/1989 |
| EP | 0 304 332 B1 | 2/1989 |
| JP | 08073344 A | 9/1994 |
| WO | WO 87/07292 | 2/1987 |
| WO | WO 90/09428 | 8/1990 |
| WO | 90/09440 | 8/1990 |
| WO | WO 90/09440 | 8/1990 |
| WO | WO 94/21383 | 9/1994 |
| WO | WO 97/23606 | 7/1997 |
| WO | 97/39116 | 10/1997 |
| WO | WO 97/39116 | 10/1997 |

OTHER PUBLICATIONS

Showell, Michael S. (editor), "Powdered Detergents"; Surfactant Science Series; 1998; vol. 71; pp. 140–142; Marcel Dekker.

* cited by examiner

*Primary Examiner*—Patricia Leith
(74) *Attorney, Agent, or Firm*—Elias Lambiris; Jason Garbell

(57) ABSTRACT

The invention relates to an enzyme-containing granule comprising a core unit and a shell unit, wherein the core unit comprises the enzyme and is enclosed in a shell unit which is substantially enzyme-free, the ratio between the diameter of the granule and the diameter of the core unit being at least 1.1. Also processes for producing such granules and use of the granules are disclosed.

3 Claims, No Drawings

ENZYME GRANULATE

CROSS-REFERENCE TO RELATED APPLICATIONS

This application claims priority under 35 U.S.C. 119 of Danish applications PA 1999 001415 filed Oct. 1, 1999 and PA 2000 00251 filed Feb. 17, 2000, and of U.S. Provisional application 60/158,270 filed Oct. 7, 1999 and 60/185,206 filed Feb. 25, 2000, the contents of which are fully incorporated herein by reference.

FIELD OF THE INVENTION

The invention relates to novel enzyme granule products containing a concentrated enzyme core and to processes for the production of the enzyme granules.

BACKGROUND OF THE INVENTION

Known enzyme granule formulation technologies include:

a) Spray dried products, wherein a liquid enzyme-containing solution is atomised in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140–142; Marcel Dekker).

b) Layered products, wherein the enzyme is coated as a layer around a pre-formed inert core particle, wherein an enzyme-containing solution is atomised, typically in a fluid bed apparatus wherein the pre-formed core particles are fluidised, and the enzyme-containing solution adheres to the core particles and dries up to leave a layer of dry enzyme on the surface of the core particle. Particles of a desired size can be obtained this way if a useful core particle of the desired size can be found. This type of product is described in e.g. WO 97/23606.

c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme. (Michael S. Showell (editor); *Powdered detergents*; Surfactant Science Series; 1998; vol. 71; page 140–142; Marcel Dekker)

e) Prilled products or, wherein an enzyme powder is suspended in molten wax and the suspension is sprayed, e.g. through a rotating disk atomiser, into a cooling chamber where the droplets quickly solidify (Michael S. Showell (editor); *Powdered detergents*; Surfactant Science Series; 1998; vol. 71; page 140–142; Marcel Dekker). The product obtained is one wherein the enzyme is uniformly distributed throughout an inert material instead of being concentrated on its surface. Also U.S. Pat. No. 4,016,040 and U.S. Pat. No. 4,713,245 are documents relating to this technique f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of the enzyme, fillers and binders etc. are mixed with cellulose fibres to reinforce the particles to give the so-called T-granulate. Reinforced particles, being more robust, release less enzymatic dust (vide infra).

DRAWINGS

No drawings

SUMMARY OF THE INVENTION

The present invention relates to an enzyme-containing granule comprising a core unit and a shell unit, wherein the core unit comprises the enzyme and is enclosed in a shell unit which is substantially enzyme-free, the ratio between the diameter of the granule and the diameter of the core unit being at least 1.1.

In a second aspect, the invention relates to a process for preparing enzyme core units and finished enzyme granules, comprising the enzyme core unit and the shell unit. The invention further relates to compositions comprising the enzyme granule such as foodstuff/baking/flour/dough compositions or detergent composition and the use of such compositions in application.

In further aspects the invention relates to specific processes for preparing enzyme containing core units.

DETAILED DESCRIPTION OF THE INVENTION

Definitions

The phrase "ratio between the diameter of the granule and the diameter of the core unit and" (hereinafter abbreviated DG/Dc) as used herein is to be understood as the diameter of the granule comprising a core unit and a shell unit divided by the diameter of the core unit only. If for example a core unit having a diameter of 100 $\mu$m is coated with a coating layer 200 $\mu$m thick; the granule would have a diameter of (200+100+200)=500 $\mu$m and $D_G/D_C$ is 500 $\mu$m/100 $\mu$m=5. The term "activity" when used in reference to an enzyme preparation or with reference to an enzyme granule or an enzyme core is a relative measure of the ability of the enzyme in the preparation, granule or core to react with a standard substrate at fixed standard conditions. Activity is measured in units which is defined as $\mu$moles of substrate reacted per minute per gram of the measured sample at fixed standard conditions (herein after "a standard assay"). The activity is also a measure of the amount of active enzyme protein. An enzyme has a specific activity which is the activity of the pure enzyme protein in the standard assay. The specific activity is also measured in units which is defined as $\mu$moles of substrate reacted per minute per gram of pure enzyme at fixed standard conditions. When the specific activity of an enzyme is known the amount of pure enzyme protein in a sample can be calculated. If a 1 gram sample of a pure enzyme react with 100 $\mu$moles of a substrate per minute in a standard assay, the specific activity of the enzyme is 100 Units per gram pure enzyme. If a 1 gram sample of unknown enzyme activity reacts with 50 μmoles of a substrate per minute in the standard assay, the activity of the sample is 50 Units per gram and there is 0.5 g of pure enzyme protein in the sample.

It is to be understood that the term "size" of particles or granulates covers the diameter of a particle measured in the longest dimension of the particle or granulate. Also, the mean size of granules is to be understood as the mean diameter of granules manufactured by the process of the invention measured in the longest dimension of the particles. The term "particle size distribution" is meant to be understood the range of sizes of granules resulting from a particular process; the spectrum or gradient distribution of granules with regards to their diameter.

The particle size distribution (PSD) can be expressed in terms of the mass mean diameter of the individual particles. A mean mass diameter of D50 is the diameter at which 50% of the granules, by mass, have a smaller diameter, while 50% by mass have a larger diameter. The values D10 and D90 are the diameters at which 10% and 90%, respectively, of the granules, by mass, have a smaller diameter than the value in question. The "span" indicates the breadth of the PSD and is expressed as:

(D90−D10)/D50.

For purposes of the present invention, the particle size distribution is normally as narrow as possible. The span of a granulate product according to the invention is therefore typically not more than about 2.5, preferably not more than about 2.0, more preferably not more than about 1.5, and most preferably not more than about 1.0 such as between 0.1 to 0.9.

The terms "particle" and "granulate" or "granule" are to be understood as predominantly spherical or near spherical structures of a macromolecular size.

The term "substantially enzyme free" as used herein about a shell unit means that there less than 5 mg of enzyme per gram shell.

The term "Rayleigh Atomizer" is to be understood as an atomizer capable of producing droplets of liquid having a low SPAN value (usually SPAN values below 1.5 can be obtained such as between 0.9–1.3), said atomizer characterized by comprising a spraying member and a surface member comprising at least one bore hole. In a preferred embodiment the Rayleigh Atomizer is a rotating atomizing device wherein a liquid is atomized by distributing the liquid onto the inner surface of a rotating hollow cylinder comprising bore holes, the liquid forming droplets by passing the cylinder wall through the bore holes. Such an atomizer is described in WO 94/21383 claims 9–30 and FIGS. 1–18 and methods for atomizing in claims 1–8 all incorporated herein by reference. The principles and mechanics of Rayleigh atomization are known to the art.

The Granule

In enzyme granules of the invention, enzymatic activity is concentrated into a central core unit surrounded a shell unit or coating which is substantially enzyme free. The core unit is smaller than core units known to the art and the shell unit is thicker than shell units known to the art and in order to provide enzyme granules having a total activity useful in established applications of enzyme granules the enzyme activity in the core unit is considerably augmented. The smaller enzyme cores of the invention, which can be prepared having a very narrow particle size distribution provides new and flexible preparation ways of controlling the activity by independently varying the size of the enzyme core and the thickness of the surrounding shell. Moreover, the enzyme granules of the invention have environmentally advantageous properties such as low dust and odour levels, reduced contents of granulate additive and improved storage stability of the enzyme. The products may have a natural white colour circumventing the need for expensive and environmentally antagonistic pigments such as titanium dioxide pigments in additional coatings.

The granule of the invention is characterised by having a structure wherein $D_G/D_C$ is at least 1.1, which means that the thickness of the shell unit is at least 5% of the core unit diameter. The more the enzyme activity can be concentrated in the core unit, the smaller the core unit can be made, and the thicker the shell unit can be made, when preparing a granule of a desired fixed activity. Smaller core units improves the granule properties and increase flexibility in the preparation of the granules. Accordingly in a preferred embodiment $D_G/D_C$ for the granule is at least 1.5, preferably at least 2, more preferably at least 2.5, more preferably at least 3, most preferably at least 4. $D_G/D_C$ is however preferably below about 100, preferably below about 50, more preferably below 25, and most preferably below 10. A most preferred range for $D_G/D_C$ is about 4 to about 6.

In certain embodiments the enzyme granule, the enzyme core further comprises a film layer around the core unit to protect the core unit from components present in the shell unit. This protective outer film layer may also serve other purposes such as for stability of both the enzyme itself and the structurally integrity of the unit, and for storage purposes.

The Enzyme Core Unit

Enzymes of the present invention are situated within the enzyme core unit. The enzyme core unit is designed to be as small in size as possible but to include a necessary amount of enzyme for the purpose of the granulate, as well as components useful for providing structural stability of the enzyme core unit and/or physical and chemical stability of the enzyme itself. Thus, the enzyme core unit will comprise at least one enzyme and optionally one or more excipients or additives.

Given that one advantage sought after by the present invention is to limit the dispersion or distribution of expensive additives, such as enzyme stabilising agents only to a small fraction of the granulate, preferred embodiments of the granulate limit the size of the core unit, in terms of its relative mass, to comprise up to about 30%, such as up to about 20% of the overall mass of the granulate, such up to about 15%, preferably up to about 10%, such as up to about 5% of the overall mass.

The size of the enzyme core unit, in terms of its diameter in its longest dimension, in preferred embodiments of the invention, is no more than 1000 μm, preferably no more than 700 μm or 600 μm, preferably between 100 and 500 μm, such as between 100 and 400 μm, preferably between 200 and 300 μm. In relation to the overall diameter of the granulate, its diameter is intended to be less than that of the shell unit and being the diminutive of the two units with regards to the overall diameter of the of the granulate.

The intention is to concentrate the enzyme content to a small central fraction of the overall granulate. This small fraction, herein termed the enzyme core unit, although intended to be small in size, must at least be large enough to prevent its agglomeration with other enzyme core units during the granulation process by shell coating components. To prevent agglomeration of the enzyme core unit during further processing however, the size of the enzyme core unit is preferably greater than 50 μm, such as greater than 100 μm. This may correspond to an enzyme core unit of at least 1% by weight of the total mass, such as at least 2%, such as at least 5% or 10% of the total mass. In a preferred embodiment the core constitutes between 1 to 5% w/w of the granule.

An integral feature of the present invention is that enzyme activity is limited solely to the core unit. No other moiety or component of the granule as defined by this invention is intended to contain enzymes. As is known by the person skilled in the art however, the enzyme may be dispersed or diffused elsewhere during the use of the final granulate.

The physical state of the enzyme core can be that of a solid, liquid, or gel.

Preferable embodiments of the invention comprise a solid enzyme core unit. In one embodiment of the invention, the enzyme core unit is solid when encased in its shell unit. Thereafter, the enzyme granule can be heated above the melting point of the binders or other components of the enzyme core so as to cause these components to diffuse into the inner parts of the shell unit resulting in an increase porosity of the enzyme core. This will in turn increase the solubility of the core unit.

Enzymes

The enzyme in the context of the present invention may be any enzyme or combination of different enzymes. Accordingly, when reference is made to "an enzyme" this will in general be understood to include both a single enzyme and a combination of more than one enzyme.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk), EP 525,610 (Solvay) and WO 94/02618 (Gist-Brocades NV). The enzyme classification employed in the present specification and claims is in accordance with *Recommendations* (1992) *of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)], while preferred transferases are transferases in any of the following sub-classes:
a) Transferases transferring one-carbon groups (EC 2.1);
b) Transferases transferring aldehyde or ketone residues (EC 2.2); acyltransferases (EC 2.3);
c) Glycosyltransferases (EC 2.4);
d) Transferases transferring alkyl or aryl groups, other than methyl groups (EC 2.5); and
e) Transferases transferring nitrogeneous groups (EC 2.6).
A most preferred type of transferase in the context of the invention is a transglutaminase (protein-glutamine γ-glutamyltransferase; EC 2.3.2.13).
Further examples of suitable transglutaminases are described in WO 96/06931 (Novo Nordisk A/S).
Preferred hydrolases in the context of the invention are:
Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses):
α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose α-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), arabinan endo-1,5-α-L-arabinosidases (3.2.1.99), lactases (3.2.1.108), chitosanases (3.2.1.132) and xylose isomerases (5.3.1.5).

Examples of commercially available oxidoreductases (EC 1.-.-.-) include Gluzyme™ (enzyme available from Novo Nordisk A/S).

Examples of commercially available proteases (peptidases) include Kannase™, Everlase™, Esperase™, Alcalase™, Neutrase™, Durazym™, Savinase™, Pyrase™, Pancreatic Trypsin NOVO (PTN), Bio-Feed™ Pro and Clear-Lens™. Pro (all available from Novo Nordisk A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipoprime™ Lipolase™, Lipolase™ Ultra, Lipozyme™, Palatase™, Novozym™ 435 and Lecitase™ (all available from Novo Nordisk A/S).

Other commercially available lipases include Lumafast™ (*Pseudomonas mendocina* lipase from Genencor International Inc.); Lipomax™ (*Ps. pseudoalcaligenes* lipase from Gist-Brocades/Genencor Int. Inc.; and *Bacillus* sp. lipase from Solvay enzymes. Further lipases are available from other suppliers.

Examples of commercially available carbohydrases include Alpha-Gal™, Bio-Feed™ Alpha, Bio-Feed™ Beta, Bio-Feed™ Plus, Bio-Feed™ Plus, Novozyme™ 188, Celluclast™, Cellusoft™, Ceremyl™, Citrozym™, Denimax™, Dezyme™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novo Nordisk A/S). Further carbohydrases are available from other suppliers.

The enzyme content (calculated as pure enzyme protein) in a core unit of the invention will typically be in the range of from about 20% to 100% by weight of the enzyme core unit, preferably no less than 25%, such as no less than 30%, 35%, 40%, 45%, 50%, 55%, 60%, 65%, 70%, 75%, 80%, 85% 90%, or 95% by weight.

However some enzymes have a very high specific activity so that less enzyme protein by weight is required to maintain a high activity of the core unit. Accordingly for e.g. a protease a preferred core activity is at least 60 KNPU per gram core, more preferably at least 100 KNPU, more preferably at least 200 KNPU or most preferably at least 250 KNPU per gram core. The unit for protease activity used herein is Kilo Novo Protease Units per gram of sample (KNPU/g). The enzyme activity is determined in a standard assay by measuring for a given amount of core the formation rate ($\mu$mol/minute) of free amino groups liberated from digestion of di-methyl-casein (DMC) in solution by the enzyme. The formation rate is monitored by recording the linear development of absorbance at 420 nm of the simultaneous reaction between the formed free amino groups and added 2,4,6-tri-nitro-benzene-sulfonic acid (TNBS). The digestion of DMC and the colour reaction is carried out at 50° C. in a pH 8.3 boric acid buffer with a 9 min. reaction time followed by a 3 min. measuring time. A folder AF 220/1 is available upon request from Novo Nordisk A/S, Denmark, which folder is hereby incorporated by reference.

Generally, for all enzymes a preferred core activity is at least the activity which can be measured for a core having more than 20% w/w of a known enzyme using known methods.

Preferably the enzyme in a crystalline or amorphous form is homogeneously distributed or dispersed within the core unit.

The enzyme content of a finished granule (coated) will be considerably lower. The protease content in a finished granule will for example typically be in the range of 1–20 KNPU/g, while for an. α-amylase an activity of 10–500 KNU/g will be typical. For e.g. lipases, an activity in the range of 50–400 KLU/g will normally be suitable.

The choice of enzyme or enzymes is dependent on the end purpose of the granulate. The term "enzyme" and some preferred examples of the term were defined earlier (vide supra). One or more enzymes or enzyme types, optionally requiring co-enzymes, optionally as part of a multi-enzyme complex, optionally as a zymogen, can be in the enzyme core unit.

One embodiment of this aspect of the invention comprises a structured enzyme core unit whereby enzyme-containing particles are clustered within the enzyme core unit to form a clustered-particle core unit. Particles may each contain the same or different enzymes and may be optionally coated. An alternative embodiment of a structured enzyme core unit is that of a layered enzyme core unit whereby an a inert hydratable core particle is layered/coated, e.g. by fluid bed layering, with an enzyme-containing layer to form a layered enzyme core unit. The structured core unit may also be formed of an enzyme containing core layered with enzyme-containing layers to form a multi-layered enzyme core unit. Granules comprising of a structured core unit comprising two or more enzymes are termed co-granules. Such co-granules are commercially interesting in part because they minimise the amount shell unit materials. Typical co-granules have protease and amylase activities, but other combinations, such as protease-lipase-carbohydrase and many other combinations of 2 or 3 activities and/or enzymes are also possible. Co-granules can be as layered structures or as clustered-particle structures.

Excipients

The enzyme core unit can comprise excipients or additives, which may serve a specialised function in the core unit. Excipients may be compounds conventionally used in the art, and may be selected from the non limiting group of:

Enzyme stabilising agents. Enzyme stabilising or protective agents such as conventionally used in the field of granulation may be elements of the enzyme-containing unit. Stabilising or protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, carbonates or bicarbonates which provide a chemical scavenging effect by actively neutralising e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate or methionine. Also enzyme stabilizers may be borates, borax, formates, di- and tricarboxylic acids and reversible enzyme inhibitors such as organic compounds with sulfhydryl groups or alkylated or arylated boric acids. Examples of boron based stabilizer may be found in WO 96/21716, whereas a preferred boron based stabilizer is 4-Formyl-Phenyl-Boronic Acid or derivatives thereof described in WO 96/41859 both disclosured incorporated herein by reference. Still other examples of useful enzyme stabilizers are gelatine, casein, Poly vinyl pyrrolidone (PVP) and powder of skimmed milk. Enzyme stabilising agents may constitute be 0.01–10% w/w of the core unit, preferably 0.1–5%, e.g. 0.5–2.5% w/w of the core unit.

Solubilising agents. The solubility of the enzyme core unit is especially critical in cases where the unit is a component of detergent formulation. As is known by the person skilled in the art, many agents, through a variety of methods, serve to increase the solubility of formulations, and typical agents known to the art can be found in national *Pharmacopeia's*. Thus, the enzyme core unit may optionally comprise any agent that serves to enhance the solubility of the enzyme core unit. These agents usually cause the formulation to swell upon contact with water, or to disintegrate, rupture, burst or break open.

Inorganics, such as water soluble and/or insoluble inorganic salts such as finely ground alkali sulphate, alkali carbonate and/or alkali chloride, clays such as kaolin (e.g. Speswhite™, English China Clay), bentonites, talcs, zeolites, calcium carbonate, and/or silicates.

Binders, e.g. binders with a high melting point or indeterminately high melting points and of a non-waxy nature, e.g. polyvinyl pyrrolidone, dextrins, polyvinylalcohol, cellulose derivatives, for example hydroxypropyl cellulose, methyl cellulose or CMC. A suitable binder is a carbohydrate binder such as Glucidex 21D™ available from Roquette Freres, France.

Waxes, such as organic compounds having a melting temperature of 25–150° C., preferably 35–80° C. Suitable waxes includes Poly ethylene glycols; polypropylens or polyethylens or mixtures thereof; Nonionic surfactants; Waxes from natural sources such as Carnauba wax, Candelilla wax, bees wax, hydrogenated plant oil or animal tallow; fatty acid alcohols; mono-glycerider and/or di-glycerider; fatty acids and paraffines.

Fibre materials such as pure or impure cellulose in fibrous form. This can be sawdust, pure fibrous cellulose, cotton, or other forms of pure or impure fibrous cellulose. Also, filter aids based on fibrous cellulose can be used. Several brands of cellulose in fibrous form are on the market, e.g. CEPO™ and ARBOCELL™. Pertinent examples of fibrous cellulose filter aids are is Arbocel BFC200™ and Arbocel BC200™. Also synthetic fibres may be used as described in EP 304331 B1 and typical fibres may be made of polyethylene, polypropylene, polyester, especially nylon, polyvinylformate, poly(meth)acrylic compounds.

Cross-linking agents such as enzyme-compatible surfactants, e.g. ethoxylated alcohols, especially ones with 10 to 80 ethoxy groups. These may both be found in the shell unit and in the enzyme core unit.

Suspension agents, mediators (for boosting bleach action upon dissolution of the granule in eg a washing application) and and/or solvents may be incorporated as conventional granulating agents.

Viscosity regulating agents. Viscosity regulating agents may be present in the core unit as a reminiscence from the preparation of the core unit.

An important feature related to the smaller size of the core unit of the invention is that the volume, in which excipients are contained, is much smaller than the volume of known core units. Accordingly, for a calculated optimum concentration of an excipient in a core unit the absolute amount of excipient required to obtain this concentration is reduced. This feature reduces the manufacturing costs of a granule of the invention, because excipients often are expensive speciality chemical.

The Shell Unit

The shell unit of the invention is thicker than known shell unit and have a preferred thickness of at least 25 $\mu$m. A more referred thickness is at least 50 $\mu$m such as at least 75 $\mu$m, at least 100 $\mu$m, least 150 $\mu$m, least 200 $\mu$m, least 250 $\mu$m or most preferably at least 300 $\mu$m.

The shell unit comprises one or more conventional shell or coating components such as described in in WO 89/08694, WO 89/08695, 270 608 B1 and/or PA 1998 00876 (Danish priority application unpublished at the priority date of this invention). Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492. Especially the salt coatings described in PA 1998 00876 are useful as a shell unit in the present invention.

The components comprised in the shell unit composition may be selected from the list of excipient described, supra, in the "enzyme core unit" section. Further components may be selected the following non-limiting list of chlorine scavengers, plasticizers, pigments, lubricants (such as surfactants or antistatic agents) and fragrances.

Plasticizers useful in coating layers in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents. Examples of suitable lubricants are polyethylene glycols (PEGs) and ethoxylated fatty alcohols.

In embodiments aimed primarily at detergent formulations, different "functional" components could be added to the shell such as TAED, CMC, bleach, OBA, surfactants, perfume as well as other functional components used in detergent formulations known to the person skilled in the art. The shell may also optionally comprise functional components selected for their specific use in the foodstuffs industry, baking industry, additives industry, feed industry, detergents industry or other industries where enzyme granules can be used.

In a preferred embodiment of the invention the granule of the invention is coated with a protective coating having a high constant humidity such as described in the Danish patent application PA 1998 00876 pages 5–9, which is hereby incorporated by reference. Accordingly the shell unit should, in certain embodiments, act as a moisture and/or bleach barrier to stabilise the enzyme activity in the core unit. Furthermore, in alternative embodiments, the shell unit acts as a mechanical barrier during mechanical processes such as dosing or tabletting. In certain embodiments, the shell unit is sufficiently compressible and flexible for the enzyme core unit to withstand a tabletting process, both in a structural sense and with regards to activity. This is potentially most applicable for detergent formulations.

The shell unit, in many ways, resembles conventional shell unit or coating layers surrounding an enzyme containing core, except for the notable difference that it is thicker, preferably considerably thicker than known shell units. Also as opposed to conventional thin shell units, the shell unit of the invention contains very little enzyme. During preparation of an enzyme granule some of the enzyme in a core unit often undesirably passes or diffuses into the shell unit and may even reach the outer surface of the granule. However, in the present invention the increased thickness of the shell unit reduces the relative amount of enzyme in the shell, so that the amount of enzyme per weight of shell may be kept very low. Also by increasing the shell thickness the enzyme may be prevented from reaching the outer surface of the granule. Thus, the shell unit may be considered substantially free of enzymes in accordance with the definition used herein. The increased shell thickness of the invention reduces the amount of enzyme dust which may be released when handling the granules in a dry form, eg. as determined in the well known Heubach test method.

The shell unit provides protection to the enzyme in the core unit, because it physically separates the environment of the core unit, in which the enzyme is usually stabilised, from the environment surrounding the granule, which is usually hostile to the enzyme. Conventional thin shell units provides less protection, and it is necessary to incorporate expensive enzyme protecting agents in the shell unit, which neutralise harmful components, which penetrate from the surrounding environment through the shell unit and into the core unit. By applying a thick shell unit this process is reduced, eg. by the distance between the core unit and the surrounding environment. In a preferred embodiment addition of enzyme protecting agents to the shell unit becomes obsolete and the shell unit is substantially free of enzyme protecting agents. By using the term "substantially free" in this context it is meant that enzyme protecting agents is not intentionally added to the shell unit. However, enzyme protecting agents from the core unit may during preparation of a granule pass or diffuse from the core unit into the shell unit. Accordingly, the term means that the concentration of enzyme protecting agent in the shell unit is less than 10% w/w the concentration in the core unit. The shell unit will also protect the enzyme in the core unit, when products containing granules of the invention is processed, such as steam-pelletising of feeds. The high temperatures used in the steam process can, under certain conditions, denature the enzymes thus reducing or destroying their activity. The shell unit may comprise components that confer thermal-resistance to the shell unit or whose overall composition gives a shell unit that will melt at a temperature at which the enzyme is still fully stable. This will allow the temperature within the immediate environment of the enzyme to rise no higher than the melting point of the shell unit for a certain period of time (the time in question is also dependent on the thickness of the shell unit). Accordingly a shell unit suitable for protecting an enzyme in the core unit during a (steam) pelletising process should have a melting temperature or temperature range within 70–120° C.

An important feature of the shell unit of the invention is that the increased thickness and composition of the shell unit contributes to granule properties such as, the overall activity, size and density of the granule. Accordingly in the present invention the activity of the final granule, the size and the bulk density may be adjusted by variation in the composition and thickness of the shell unit. For a given core unit, thicker shell units and heavier shell unit compositions provides lower activity of the final granule, increased size and increased bulk density. This means that a vide range of different granules useful for different purposes and applications may be prepared using only one type of core unit. This is achievable, because variations in a thick shell unit to adjust properties like activity, size and density of a granule is possible, without seriously deteriorating the mechanical, structural or protective properties of the shell unit.

The size of the shell unit may be altered to meet the needs of the manufacturer, depending on its purpose, be it detergents, foodstuff, baking agents, animal feed or any of the other uses known by the person skilled in the art.

Moreover, density is also an important feature of the enzyme granule. In for example a detergent formulation comprising enzyme granules, an inappropriate granule density leads to separation of the detergent components leading to inconsistent performance of the product. This is highly undesirable and this issue has received much focus.

The shell, in certain embodiments, can comprise several layers, each with a special function.

In a preferred embodiment the shell has an outer layer of a liquid lubricant. The purpose of the lubricant is to grease the granule so as to increase flow ability of the granule and to further inhibit dust formation when individual granules collide during handling. The lubricant is preferably a mineral oil or a nonionic surfactant, and more preferably the lubricant is not miscible with the other shell materials.

Process for Preparing Core Units; Shell Units and Granules

In ongoing research aimed at improving enzyme granulate formulations, with regards not only to granule properties, but also equally to process design and economy of design, a conceptually new preparation process for preparing small core units of high enzyme activity surrounded by a thick shell unit has been developed. Accordingly the invention relates to a process for preparing an enzyme containing granule having a core-shell configuration, comprising the step of coating an enzyme containing core with a shell, so that the ratio between the diameter of the granule and the diameter of the core unit is at least 1.1.

In this process the preparation of a core unit may be physically separated in time and location from the process of coating the, preferably substantially enzyme free shell unit on the core unit and properties of the resulting granule may be adjusted and customised to specific applications by variation in the shell thickness and composition and by preparing core units having a narrow particle size distribution and a homogenous levels of enzyme.

When preparing enzyme granules of desired properties, a process wherein core units, which have a high or concentrated enzyme activity, are coated with a shell of an increased thickness offers several advantages:

The core unit may be prepared independently of the process of applying the shell onto the core unit, because properties such as size, activity, density, colour, enzyme dust levels, odour, mechanical and physical strength etc. of the finished granule may be adjusted by the shell unit. This means that a vide range of different granules useful for different purposes and applications may be prepared using only few basic types of core units. The process of the invention provides huge logistic advantages because the core units may be prepared independently from the coating process, and may be stably transported and stored t suitable conditions as independent physical entities or product intermediates, which upon desire may be enclosed in a coating or shelling process to produce finished granule designed for a specific application. Storage conditions would preferably be where humidity levels and temperature are controllable or, where the enzyme cores are packaged, can be stabilised for e.g. in an airtight container. In fact there may be big differences in time and location between preparation of the core units and preparation of finished granules. The time difference or time span between preparing the core units and applying the shell unit for finishing the granules may be hours (1–24 hours), days (1–7 days), weeks (1–52 weeks) and even years (1–5 years), and the process provide for preparation of the core units in one geographical area (e.g. one country) and finishing granule in another geographical area (e.g. another country). Accordingly the storage stable core units may easily be shipped at low costs to a local finishing site for application of a shell unit which meets the specific needs of the intended local market. Also the concentrated enzyme core units provide reduced storage requirements, and reduced environmental risk in the packaging, shipping and handling.

As many of the properties of the finished granule are conferred to the granule in the coating or shelling process methods for preparing core units may be chosen or developed which provides a narrow particle size distribution of the core units. Accordingly the process provides for reduced loss of enzyme activity during preparation, because the need further processing of the core units such as sieving, separating and re-circulating of over and under sized cores is reduced. Recycling processes are costly and incurs loss of active enzyme.

Energy savings are obtained by reducing recycling.

Production capacity is increased with decreasing recycle ratios.

Improved activity control. Once the activity and size of core units is determined, the activity and size of a finished granule may easily be estimated on-line by measuring the size of the finished granule.

Improved homogeneity in the finished granule activity.

Preparation of Core Units

The enzyme cores of the invention may be produced using techniques known per se in the art. Non-limiting examples of suitable techniques are spray cooling, spray drying, melt granulation and high shear granulation. A combination of more than one of these techniques may also be employed.

In one embodiment, the process for preparing core units is a spray cooling process. A spray cooling process is one wherein an enzyme is dispersed and/or dissolved in a molten substance at a temperature such as not to denature the enzyme, and this mixture is cooled to solidify the substance incorporating the enzyme. The substance is preferably organic, and has a melting temperature or melting temperature range within 20–150° C., preferably between 35–80° C. h. Such substances are frequently termed a "wax" (see Michael S. Showell (editor); *Powdered detergents*; Surfactant Science Series; 1998; vol. 71; page 140–142; Marcel Dekker).

In a spray cooling process solidification of the mixture of enzyme in melted wax is achieved by atomising the mixture into droplets and solidifying the droplets in a stream of cooling air, typically in a cooling tower, whereby enzyme core unit particles having a narrow PSD can be obtained.

The enzyme may be applied to the molten wax by mixing a preferably purified crystalline or amorphous enzyme (such as described in WO 91/09943) into the molten wax. In a more preferred embodiment the enzyme and optionally other components are in a dry powder form such as spray dried products, which is dispersed or suspended in the molten wax. Atomization of the molten wax may be achieved in a number of way, where amongst it is preferred to perform the atomization using either a high speed rotating disk atomizer, a pressure nozzle, a pneumatic nozzle or a sonic nozzle such as described in the Course Material from the Microencapsulation Seminar, held by Center for professional advancement on May 9 to May 11, 1990 in Amsterdam. The solidification of the droplets by cooling may advantageously be performed in a cooling container such as a tower, wherein the atomized dispersion or solution of enzyme in molten wax is introduced into a cold air stream in the top of the tower, and the solidification of the droplets occurs while the droplets passes through the cold air stream towards the bottom of the tower. The mixture of molten wax, enzyme and optionally other components is preferably fed to the atomizer at a temperature at least 30° C. above the temperature at which the solidification commences, in order to avoid unintended solidification and blockage in feed pipes and atomizer. The quantity and temperature of air used for cooling the molten wax mixture should be adjusted so that is able of removing sufficient heat from the molten wax mixture to enable solidification (sensible heat of the liquid, latent heat of fusion of the solid and sensible heat of the solid). In a preferred embodiment the temperature of air leaving the cooling tower is about 5° C. below the temperature of solid particles leaving the cooling tower.

The general technique of spray cooling or spray chilling is well known to the art, and may be performed using well known equipment such as described in K. Masters, Applications in the chemical industry, section 14.10.1, pp 565–566, Spray drying Handbook, 3'edition 1979 George Goodwin Ldt. London ISBN 0-7114-4924-4/John Wiley & Sons, New York.

A preferred special atomiser is a Rayleigh atomiser with which a particularly narrow particle size distribution may be obtained. One such atomiser is described in WO 94/21383. This atomiser allows for a process in which the amount of core units that must be reprocessed due to being odd sized is considerably lowered. Although a spray cooling process is a very energy efficient process in that the heat of melting is much smaller than the heat of evaporation, it is not desirable to have any significant recycling of product due to capacity limitations and the risk of possible loss of enzymatic activity.

As an alternative core units may also be prepared by a process comprising making a dispersion of enzyme and optionally other components in a molten wax, letting the wax solidify and milling/crushing the solidified wax incorporating the enzyme particles and optionally rounding the particles, e.g. in a marumerizer process.

Another preferred alternative of preparing a wax based core unit (i.e enzyme containing particle) is a process comprising
(a) dispersing or dissolving an enzyme in a molten wax,
(b) transferring the dispersion to a liquid phase, e.g. an oil, in which both the enzyme and the wax are immiscible,
(c) forming an emulsion of small droplets of enzyme-wax dispersion in the liquid phase,
(d) cooling the liquid phase and the enzyme-wax droplets to solidify the wax into particles,
(e) isolating the particles from the liquid phase.

For the purpose of the invention this type of process is denoted an emulsion granulation process.

Another possible embodiment to produce the enzyme core unit is a special spray drying process using the same or similar type of atomiser as the Spray cooling process, preferably the Rayleigh atomiser. This only requires a spray drying tower sufficiently large to allow the relatively large droplets to dry to the desired enzyme core size. This process route will result in a very efficient process; both with regards to energy and monetary investment.

In another embodiment of the invention, the enzyme core unit is produced by a melt granulation process. Melt granulation processes are known to the person skilled in the art (see *Melt agglomeration with polyethylene glycols in high shear mixers*, Torben Schaefer, The Royal Danish School of Pharmacy, 1996). It is may be preferred to add melt binder to the enzyme process prior to spray drying.

The enzyme core may be produced by a high shear granulation process in which the spray dried enzyme powder as produced by any of the preceding methods is mixed with components such as cellulose, dextrins, and sulfates before being transferred to a high shear mixer. A binder solution and sugar may be added in water until a desired mean particle size is achieved.

The enzyme core units can either be utilised directly after the preparation or they may be stored as an intermediate product, which can be processed later at the same production site or shipped to other specialised production sites, where several different products may be produced form the same enzyme core. This process is consequently very flexible compared to prior art, where only one product type might be produced at one time. In addition, the minimum feasible batch size is much smaller in the enzyme core process due to the small product hold-ups in the process. In one embodiment of the process, a thin film is applied to the enzyme core unit prior to shipping, storage, or immediate further processing to the final granule. The film layer can in certain embodiments aid in the subsequent shell coating step by comprising materials aiding in adhesion.

Application of Shell Units

Formation and application of the shell unit may also be performed using techniques known per se in the art, e.g. a mechanical coating process and/or a fluid bed coating process.

The coating step, i.e. addition of the shell to the enzyme core may be done as a pure mechanical coating process, wherein the core unit is mixed with the coating material in a mixer, such as in a Pan granulator, or as a fluid bed coating process in which the core is fluidised and a solution or dispersion of the shell material is sprayed onto the core or a combined mechanical coating and a fluid bed coating process. Both of these processes can be utilised, e.g. first fluid bed coating to enhance the enzyme core size up to a certain minimum size followed by a mechanical layering process to reach the final size, or just one of them can be utilised. In preferred embodiments of the coating process, the internal parts of the shell are produced in a fluid bed process.

A mechanical coating process may also be combined with a fluid bed drying step to enhance the production rate.

Application of Enzyme Granules

The invention also relates to compositions comprising the enzyme granule of the invention. The composition may be any composition, but preferred compositions are those intended for such in the food, baking and/or detergent industry. Accordingly the composition may be a food, bakers flour, dough or detergent composition or an additive to be incorporated in such compositions. Also the invention encompasses the use of the composition, e.g. for improving foodstuffs such as bread or for cleaning an object such as a cellulose containing fabric.

The enzyme granule, as stated above, can find application in a variety of industries. Moreover, within each industry, the granule can be customised to suit the needs of the manufacturer, the needs of the market, the needs of the end-user and the "cultural/societal" habits of local markets. One such example of customising the overall formulation of the granule to suit specific needs is for an enzyme granule that can be manipulated late in the manufacturing and processing stage in the detergents industry. The Japanese market requires a granule effective and amenable to cold water washing for short periods of time; the American market requires a granule effective and amenable to structured liquid formulations and hot tap-water temperatures; the European market requires a granule effective and amenable to hot washing temperatures and long washing times; the Southeast Asian and Asian markets requires a granule effective and amenable to hand washing using soap bars. All of these markets can be catered to more appropriately if the shell unit and final formulation are done separately or even locally. The present invention allows for this by preparing the enzyme cores independently allowing for shipping them to a multitude of processing plants to serve the multitude of requirements of specific markets.

Using Enzyme Core as Baking Additive

In a special embodiment of the invention we have found that our development of small durable enzyme containing core unit is useful in certain industry segments. In these segment the core units in themselves may be used.

Within the flour mill and the baking industry the use of enzymes is well established. For incorporation of enzyme particles in flour compositions, however, the particle size should not exceed a particle size of 200 μm. Such small particles have conventionally only been available as spray dried products. However, conventional spray dried product are usually fragile agglomerates of very small particles and tend to release enzyme dust. In some spray drying processes very small particles are formed initially in the drying step which subsequently agglomerate or glue together to form larger somewhat fragile agglomerates in the end of the spray drying process. Such agglomerated particles may preferably have a mean diameter or size in the range of 150–2000 μm. In other spray drying processes, such as using the atomizing device of WO 94/21383 smaller non-agglomerated more homogeneous particles may be produced because of the special design of the atomizer.

Accordingly, due to our development of using a Rayleigh atomizer the invention provides a spray dried or spray cooled process enzyme containing discrete particles having an average size below 200 μm.

Accordingly the present invention provides a process for preparing an enzyme containing particle comprising atomizing an enzyme containing liquid starting material by means of a Rayleigh atomizing device. The process is preferably a spray drying process, whereby the enzyme containing liquid is aqueous or spray cooling process, whereby the liquid is a wax. The invention also encompass compositions comprising enzymes core particles obtained by the process, in particular dough improver compositions comprising the enzyme core particles or flour compositions comprising the dough improver.

Concerning size, the particles of this embodiment have a low mean diameter, preferably within the range of 50–300 μm, more preferable within 50–200 μm, most preferably within 50–150 μm.

The particles, which may will have a water content of 10–15% by weight, may preferably be further dried to an even lower moisture contents such as below about 5% w/w by introducing the spray dried particles into a fluid bed drying device in which the spray dried particles is kept fluidized by an upwards stream of preferably heated and dried air evaporating excess moisture from the fluidized particles.

In the context of this embodiment, also compositions comprising the enzyme particle obtained by Rayleigh atomisation are included. preferred compositions are dough or flour compositions.

When using enzymes in the baking industry certain enzyme activities are preferred. Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases is given below.

Certain maltogenic amylases can be used for prolonging the shelf life of bread for two or more days without causing gumminess in the product. Selectively modifies the gelatinized starch by cleaving from the non-reducing end of the starch molecules, low-molecular-weight sugars and dextrins. The starch is modified in such a way that retrogradation is less likely to occur. The produced low-molecular-weight sugars improve the baked goods water retention capacity without creating the intermediate-length dextrins that result in gumminess in the finished product. The enzyme is inactivated during bread baking, so it can be considered a processing aid which does not have to be declared on the label.

The bread volume can be improved by fungal α-amylases which further provide good and uniform structure of the bread crumb.

Said α-amylases are endoenzymes that produce maltose, dextrins and glucose. Cereal and some bacterial α-amylases are inactivated at temperatures above the gelatinization temperature of starch, therefore when added to a wheat dough it results in a low bread volume and a sticky bread interior. Fungamyl has the advantage of being thermolabile and is inactivated just below the gelatinization temperature.

Enzyme preparations containing a number of pentosanase and hemi-cellulase activities can improve the handling and stability of the dough, and improves the freshness, the crumb structure and the volume of the bread.

By hydrolysing the pentosans fraction in flour, it will lose a great deal of its water-binding capacity, and the water will then be available for starch and gluten. The gluten becomes more pliable and extensible, and the starch gelatinize more easily. Pentosanases can be used in combination with or as an alternative to emulsifiers.

Detergent Compositions

The enzyme granule of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from H. lanuginosa (T. lanuginosus) as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g. from B. subtilis (Dartois et al. (1993), Biochemica et Biophysica Acta, 1131, 253–360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of B. licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™, (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from C. cinereus, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, is formulated so as to contain one or more of the enzyme granules of the invention.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or completing agent such as zeolite, diphosphate, triphosphate, phosphonate, carbonate, citrate, nitrilotriacetic acid, ethylenediaminetetraacetic acid, diethylenetriamine-pentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The enzyme of the invention may additionally be incorporated in the detergent formulations disclosed in WO 97/07202 which is hereby incorporated as reference.

EXAMPLES

The invention is illustrated by the following unlimiting examples.

Example 1

3 kg of Savinase® enzyme (a protease enzyme available from Novo Nordisk A/S-Denmark) concentrate with a solids content of 33% w/w was added 10% w/w of a dextrin binder. The enzymatic activity was approximately 98 KNPU/g in this mixture. The mixture was spray dried in a MobileMinor lab spray dryer using an 175° C. inlet air temperature, a 60° C. outlet air temperature and co-current atomization by a two-fluid nozzle to obtain a powder with an average particle size of about 20 $\mu$p. The obtained powder had an enzymatic activity of approximating 264 KNPU/g.

The obtained powder is dispersed into 1 kg of melted PEG4000 at a temperature of 58 to 60° C. The dispersion is spray cooled by atomising it in a spray cooling tower using a high speed rotational atomiser running at 9000 RPM. The obtained core units is screened to separate the fraction between 200 to 225 $\mu$m.

Example 2

Example 1 was repeated except that the a high speed rotational atomiser was replaced with a Rayleigh atomiser as disclosed in WO 94/21383, example 1, page 19, lines 12–36 in the spray cooling step. Also the Savinase® was replaced with a protein mixture (soy protein) and the PEG 4000 was replaced with a Lutensol AT-80 wax. The protein load was 40 wt %. Upon measuring the obtained particle size distribution by a Malvern laser instrument the following result were obtained:

| Property/RPM atomizer | 3300 | 4300 |
| --- | --- | --- |
| D10, $\mu$m | 206 | 199 |
| D50, $\mu$m | 320 | 273 |
| D90, $\mu$m | 464 | 387 |
| Span | 0.81 | 0.69 |

Using a screen analysis the equivalent data on the same samples the following results were obtained:

| Property/RPM atomizer | 3300 | 4300 |
| --- | --- | --- |
| D10, $\mu$m | 203 | 185 |
| D50, $\mu$m | 306 | 266 |
| D90, $\mu$m | 397 | 350 |
| Span | 0.63 | 0.62 |

It is clearly seen from the above data that a very narrow size distribution is obtained even with the high protein load. The desired mean particle size may simply be obtained by adjusting the rotational speed of the atomizer. This enables a simple way of obtaining enzyme cores of a desired size and also having a narrow PSD and enables controlling the final enzyme activity of the finished enzyme granule comprising the core and the shell.

Example 3

Example 1 was repeated except for the spray cooling step, which was replaced by a melt granulation process and the enzyme powder was replaced with a commercially available spray dried soy protein powder (Soy-Co-Mill). 350 g of this powder was mixed with 95 g PEG 4000 chips and was added to a vertical high shear mixer (Mi—Mi-Pro from Pro-c-ept NV, Belgium). The powder temperature was raised to 66° C. using 1500 rpm impeller speed and 5600 rpm chopper speed. The obtained enzyme core particles was very compact and spherical, which greatly improves the later coating steps where the shell is supplied. A small amount of not agglomerated powder may stick to the surface of the particles if they are allowed to solidify in a non-moving system. Consequently, it will be preferred industrially to use a fluid bed cooler to solidify and to classify the obtained enzyme cores units.

Example 4

Example 3 was repeated with the exception that the soy protein powder was replaced by a spray dried enzyme powder made as in example 1, wherein the dextrin binder was added to the enzyme concentrate before spray drying is replaced by PEG 4000. This gave an efficient way of distributing a melt binder into the a spray dried powder before the melting and mixing process.

Example 5

Example 1 was repeated except for the spray cooling step which was replaced by a high shear granulation process in which the spray dried enzyme powder was mixed with 10% w/w cellulose fibres, 10% w/w dextrin binder. Sodium sulfate salt was added up to 1005 w/w. This mixture was transferred to a horizontal 50 L high shear mixer and mixed at under addition of a binder solution of having 5% w/w dextrin and 5% w/w sugar in water solution until a mean particle size of about 200 μm was achieved. The wet core units was subsequently dried in a fluid bed using 90° C. inlet temperature until the product temperature reached 60° C. The dried product is screened to obtain core units in the range from 180 μm to 250 μm. The resulting enzymatic activity was be approximately 14 KNPU/g.

Example 6

Example 1 was repeated except for the spray cooling step which was replaced by a emulsion granulation process wherein 100 g of the spray dried powder was dispersed into 100 g of a melted PEG4000 wax. This dispersion was subsequently emulsified using an Ultra Turrax blender into about one liter of mineral oil (Whiteway T15) heated to 65° C. The size of the formed droplets of enzyme-wax dispersion in oil was controlled by the speed of the blender and the addition of an emulsifying agent (SPAN 80 which is a Sorbitan mono-9-octadecenoate (Monoester of oleic acid and hexitol anhydrides derived from sorbitol). When the desired droplet size was achieved the oil was cooled to ambient temperature, and the solidified particle were filtered from the oil. The formed core unit was calculated to about 132 KNPU/g. The obtained enzyme core particles was very compact, had a narrow PSD and a large number of these was perfect spheres, which greatly improves the later coating steps where the shell is supplied. This is due to the long time available for the surface tension to form the shape of the particle and the very low shear excerpted on the droplet during solidification.

Example 7

A charge of 8 kg enzyme core produced as described in Example 5 was added to a fluid bed coater (Aeoromatic-Fielder Precision Coater. Size MP ⅔) to study the feasibility of such a fluid bed process for the initial coating of enzyme core. The aim of this study is to test the feasibility of the process to coat such a small enzyme cores without any agglomeration.

The initial properties of enzyme core were:

| Property | value |
| --- | --- |
| D10 | 185 μm |
| D50 | 218 μm |
| D90 | 251 μm |
| Span | 0.30 |
| Bulk density | 0,797 g/ml |
| Tapped density | 1,10 g/ml |
| Particle density | 2,22 g/ml |
| Savinase ® activity | 14,32 KNPU/g |

In the process following coating layers are applied:

| Coating layers | Amount applied |
| --- | --- |
| additional enzyme layer | 2537 g |
| 2. layer: sodium sulphate + water | 7850 g |
| 3. layer: HPMC + PEG400 + water | 1600 g |
| 4. layer: PEG 4000 + water | 250 g |

The processing conditions applied: 125° C. inlet air temperature and 50° C. product temperature.
The final properties of the coated enzyme core were:

| Property | value |
| --- | --- |
| D10 | 190 μm |
| D50 | 241 μm |
| D90 | 291 μm |
| Span | 0.42 |
| Bulk density | 1,00 g/ml |
| Tapped density | 1,05 g/ml |
| Particle density | 1,82 g/ml |
| Savinase activity | 15,00 |

The tapped density is measured by tapping a known mass of powder in a rigid container a specified number of times (typically 100–1000 times) and measuring the final volume of the powder. The tapped density is the ratio of the volume to the mass. The tapping is done by letting the powder container freely fall a specified distance (1–10 mm) on a hard surface. HPMC is Hydroxy-propyl-methyl-cellulose.

The results shows that it is surprisingly possible to coat such small core units without the core units agglomerating in the process.

Example 8

In this example the enzyme cores was produced by spray drying directly from a liquid concentrate using a Rayleigh atomiser as disclosed in WO 94/21383, example 1, page 19, lines 12–36. The liquid concentrates was formulated to achieve desired properties such as strength, viscosity and drying properties.
Following formulations was used:
Test 1: 2500 1 enzyme concentrate A, 1750 kg calciumcarbonate, 750 kg sugar and 400 kg water.
Test 2: 2000 1 enzyme concentrate B, 1500 kg calciumcarbonate, 91 kg sugar and 49 kg water.
Test 3: 1400 1 enzyme concentrate C, 350 kg calciumcarbonate, 91 kg sugar and 49 kg water.
Using a screen analysis on the obtained enzyme cores to measure the PSD the following results were obtained:

| Property/RPM atomizer | Test 1: 4000 RPM | Test 2: 4000 RPM | Test 3: 4000 |
| --- | --- | --- | --- |
| D10, μm | 99 | 98 | 74 |
| D50, μm | 192 | 192 | 201 |
| D90, μm | 321 | 400 | 283 |
| Span | 1,16 | 1,58 | 1,04 |

These results shows the distribution of the unscreened product obtained directly from the spray drying including the fines fraction from the filter.
Upon measuring the particle densities and enzymatic strengths of the spray dried enzyme cores the following results were obtained:

| Test/Property | Particle density g/ml | KNPU(S)/g |
|---|---|---|
| Test 1 | 1,971 | 21,7 |
| Test 2 | 1,780 | 37,2 |
| Test 3 | 1,360 | 122 |

The produced particles was essential spherical and compact. The latter is seen from the true density data in Table 4. Current enzyme granulate from a high shear granulation process and having a comparable enzymatic strength has a true density which is very close to 1,9 g/ml. These results also show that using the Rayleigh atomiser it is possible in a stray drying process to produce strong non-agglomerated particles having a low size and a narrow PSD, which may suitable be used e.g. as dough improver.

What is claimed is:

1. A granulated enzymatic product comprising a multiplicity of enzyme granules, wherein the enzyme-containing granules comprise a core unit and a shell unit, wherein the core unit comprises the enzyme and is enclosed in a shell unit which is substantially enzyme-free, and the enzyme content in the core unit, calculated as pure enzyme protein, is in the range of from about 20% to 100% by weight of the enzyme core unit, wherein the ratio between the diameter of the granule and the diameter of the core unit is at least 1.1: wherein the size of the enzyme core unit, in terms of its diameter in its longest dimension, is no more than 1000 $\mu$m, and wherein the enzyme core units have a particle size distribution such that the ratio (D90–D10)/D50 is not more than about 2.5.

2. A granulated enzymatic product comprising a multiplicity of enzyme granules, wherein the enzyme-containing granules comprise a core unit and a shell unit, wherein the core unit comprises the enzyme and is enclosed in a shell unit which is substantially enzyme-free, and the enzyme content in the core unit, calculated as pure enzyme protein, is in the range of from about 20% to 100% by weight of the enzyme core unit, wherein the ratio between the diameter of the granule and the diameter of the core unit is at least 1.1: wherein the size of the enzyme core unit, in terms of its diameter in its longest dimension, is no more than 1000 $\mu$m, and wherein the enzyme core units have a particle size distribution such that the ratio (D90–D10)/D50 is not more than about 1.5.

3. A granulated enzymatic product comprising a multiplicity of enzyme granules, wherein the enzyme-containing granules comprise a core unit and a shell unit, wherein the core unit comprises the enzyme and is enclosed in a shell unit which is substantially enzyme-free, and the enzyme content in the core unit, calculated as pure enzyme protein, is in the range of about 20% to 100% by weight of the enzyme core unit, wherein the ratio between the diameter of the granule and the diameter of the core unit is at least 1.1: wherein the size of the enzyme core unit, in terms of its diameter in its longest dimension, is no more than 1000 $\mu$m, and wherein the enzyme core units have a particle size distribution such that the ratio (D90–D10)/D50 is not more than about 1.0.

* * * * *